United States Patent
Mahler et al.

(10) Patent No.: US 11,001,738 B2
(45) Date of Patent: *May 11, 2021

(54) COMPOSITIONS COMPRISING 2,3-DICHLORO-1,1,1-TRIFLUOROPROPANE, 2-CHLORO-1,1,1-TRIFLUOROPROPENE, 2-CHLORO-1,1,1,2-TETRAFLUOROPROPANE OR 2,3,3,3-TETRAFLUOROPROPENE

(71) Applicant: THE CHEMOURS COMPANY FC, LLC, Wilmington, DE (US)

(72) Inventors: Barry Asher Mahler, Glen Mills, PA (US); Mario Joseph Nappa, Leesburg, FL (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/747,266

(22) Filed: Jan. 20, 2020

(65) Prior Publication Data

US 2020/0199428 A1    Jun. 25, 2020

Related U.S. Application Data

(60) Continuation of application No. 16/244,609, filed on Jan. 10, 2019, now Pat. No. 10,584,270, which is a
(Continued)

(51) Int. Cl.
*C09K 5/04* (2006.01)
*C07C 17/04* (2006.01)
*C07C 17/087* (2006.01)
*C07C 17/20* (2006.01)
*C07C 17/25* (2006.01)
(Continued)

(52) U.S. Cl.
CPC ............ *C09K 5/044* (2013.01); *A62D 1/0028* (2013.01); *A62D 1/0057* (2013.01); *A62D 1/0092* (2013.01); *B01F 17/0035* (2013.01); *B01F 17/0085* (2013.01); *C07C 17/04* (2013.01); *C07C 17/087* (2013.01); *C07C 17/204* (2013.01); *C07C 17/206* (2013.01); *C07C 17/23* (2013.01); *C07C 17/25* (2013.01); *C07C 19/08* (2013.01); *C07C 19/10* (2013.01); *C07C 19/12* (2013.01); *C07C 21/04* (2013.01); *C07C 21/18* (2013.01); *C08J 9/144* (2013.01); *C08J 9/146* (2013.01); *C08J 9/149* (2013.01); *C09K 3/00* (2013.01); *C09K 3/30* (2013.01); *C09K 5/045* (2013.01); *C09K 5/048* (2013.01); *C09K 21/08* (2013.01); *C11D 7/30* (2013.01); *H01B 3/56* (2013.01); *C08J 2203/14* (2013.01); *C08J 2203/142* (2013.01); *C08J 2203/144* (2013.01); *C08J 2203/164* (2013.01); *C09K 2205/12* (2013.01); *C09K 2205/122* (2013.01); *C09K 2205/126* (2013.01); *C09K 2205/22* (2013.01)

(58) Field of Classification Search
CPC .......... C09K 5/044; C09K 3/30; C09K 5/045; C09K 2205/22; C09K 2205/12; C09K 2205/122; C09K 2205/126; C09K 21/08; C09K 3/00; C09K 5/048; A62D 1/0057; A62D 1/0028; A62D 1/0092; B01F 17/0085; B01F 17/0035; C11D 7/30; C07C 17/04; C07C 17/087; C07C 17/204; C07C 17/206; C07C 17/25; C07C 19/08; C07C 19/10; C07C 19/12; C07C 21/04; C07C 21/18; C07C 17/23; C08J 9/144; C08J 9/149; C08J 2203/144; C08J 2203/164; C08J 2203/14; C08J 2203/142; C08J 9/146
USPC ............... 252/67, 2, 78.1, 364, 571; 62/529; 510/461; 516/8, 12
See application file for complete search history.

(56) References Cited

U.S. PATENT DOCUMENTS

| | | | |
|---|---|---|---|
| 5,006,568 A | 4/1991 | Fukazawa et al. | |
| 5,316,690 A | 5/1994 | Li | |

(Continued)

FOREIGN PATENT DOCUMENTS

| | | | |
|---|---|---|---|
| EP | 2 107 048 A1 | 10/2009 | |
| EP | 2 149 543 A1 | 2/2010 | |

(Continued)

OTHER PUBLICATIONS

PCT International Search Report and Written Opinion dated Nov. 10, 2009.
(Continued)

*Primary Examiner* — Douglas J McGinty

(57) ABSTRACT

Disclosed are compositions comprising HCFC-243db, HCFO-1233xf, HCFC-244db and/or HFO-1234yf and at least one additional compound. For the composition comprising 1234yf, the additional compound is selected from the group consisting of HFO-1234ze, HFO-1243zf, HCFC-243db, HCFC-244db, HFC-245cb, HFC-245fa, HCFO-1233xf, HCFO-1233zd, HCFC-253fb, HCFC-234ab, HCFC-243fa, ethylene, HFC-23, CFC-13, HFC-143a, HFC-152a, HFC-236fa, HCO-1130, HCO-1130a, HFO-1336, HCFC-133a, HCFC-254fb, CHF=CHCl, HFO-1141, HCFO-1242zf, HCFO-1223xd, HCFC-233ab, HCFC-226ba, and HFC-227ca. Compositions comprising HCFC-243db, HCFO-1233xf, and/or HCFC-244db are useful in processes to make HFO-1234yf. Compositions comprising HFO-1234yf are useful, among other uses, as heat transfer compositions for use in refrigeration, air-conditioning and heat pump systems.

19 Claims, 1 Drawing Sheet

Related U.S. Application Data division of application No. 15/270,074, filed on Sep. 20, 2016, now Pat. No. 10,214,669, which is a division of application No. 14/503,765, filed on Oct. 1, 2014, now Pat. No. 9,486,657, which is a division of application No. 12/937,661, filed as application No. PCT/US2009/043118 on May 7, 2009, now Pat. No. 8,877,086.

(60) Provisional application No. 61/126,810, filed on May 7, 2008.

(51) Int. Cl.

| | | |
|---|---|---|
| C07C 19/08 | (2006.01) | |
| C07C 19/10 | (2006.01) | |
| C07C 19/12 | (2006.01) | |
| C07C 21/04 | (2006.01) | |
| C07C 21/18 | (2006.01) | |
| C08J 9/14 | (2006.01) | |
| C09K 3/30 | (2006.01) | |
| A62D 1/00 | (2006.01) | |
| B01F 17/00 | (2006.01) | |
| C09K 3/00 | (2006.01) | |
| C11D 7/30 | (2006.01) | |
| H01B 3/56 | (2006.01) | |
| C07C 17/23 | (2006.01) | |
| C09K 21/08 | (2006.01) | |

(56) References Cited

U.S. PATENT DOCUMENTS

| | | | |
|---|---|---|---|
| 5,705,716 A | 1/1998 | Li | |
| 6,244,055 B1 | 6/2001 | Hanson et al. | |
| 6,299,792 B1 | 10/2001 | Feiring et al. | |
| 6,329,559 B1 | 12/2001 | Sievert et al. | |
| 6,472,573 B1 | 10/2002 | Yamamoto et al. | |
| 6,759,381 B1 | 7/2004 | Johnson et al. | |
| 7,569,170 B2* | 8/2009 | Minor | A62D 1/0057 |
| | | | 264/53 |
| 7,641,809 B2 | 1/2010 | Leck et al. | |
| 7,803,283 B2 | 9/2010 | Pham et al. | |
| 8,034,251 B2 | 10/2011 | Merkel et al. | |
| 8,076,521 B2 | 12/2011 | Elsheikh et al. | |
| 8,147,709 B2 | 4/2012 | Mahler et al. | |
| 8,252,965 B2 | 8/2012 | Merkel et al. | |
| 8,263,817 B2 | 9/2012 | Nappa et al. | |
| 8,388,857 B2 | 3/2013 | Elsheikh et al. | |
| 8,398,882 B2* | 3/2013 | Rao | C07C 17/25 |
| | | | 252/67 |
| 8,454,853 B2 | 6/2013 | Van Horn et al. | |
| 8,877,086 B2 | 11/2014 | Mahler et al. | |
| 9,051,500 B2* | 6/2015 | Nappa | A62D 1/00 |
| 9,486,657 B2 | 11/2016 | Mahler et al. | |
| 9,598,621 B2 | 3/2017 | Minor et al. | |
| 9,650,551 B2 | 5/2017 | Collier et al. | |
| 10,214,669 B2 | 2/2019 | Mahler et al. | |
| 10,584,270 B2* | 3/2020 | Mahler | C07C 17/206 |
| 2005/0199376 A1 | 9/2005 | Lee | |
| 2005/0211949 A1 | 9/2005 | Bivens et al. | |
| 2005/0228202 A1 | 10/2005 | Nappa et al. | |
| 2005/0233932 A1 | 10/2005 | Singh et al. | |
| 2006/0106263 A1 | 5/2006 | Miller et al. | |
| 2006/0185972 A1 | 8/2006 | Balthasart et al. | |
| 2006/0243944 A1* | 11/2006 | Minor | C08J 9/149 |
| | | | 252/67 |
| 2006/0243945 A1 | 11/2006 | Minor et al. | |
| 2007/0007488 A1 | 1/2007 | Singh et al. | |
| 2007/0010592 A1 | 1/2007 | Bowman et al. | |
| 2007/0096053 A1 | 5/2007 | Nair et al. | |
| 2007/0108403 A1 | 5/2007 | Sievert et al. | |
| 2007/0112228 A1 | 5/2007 | Mukhopadhyay et al. | |
| 2007/0187639 A1 | 8/2007 | Leck et al. | |
| 2007/0197842 A1 | 8/2007 | Mukhopadhyay et al. | |
| 2007/0245759 A1 | 10/2007 | Sedlak et al. | |
| 2007/0258909 A1 | 11/2007 | Mahaut et al. | |
| 2008/0058562 A1 | 3/2008 | Petrov et al. | |
| 2008/0098751 A1 | 5/2008 | Terada | |
| 2008/0098755 A1 | 5/2008 | Singh et al. | |
| 2009/0030244 A1 | 1/2009 | Merkel et al. | |
| 2009/0124837 A1 | 5/2009 | Mukhopadhyay et al. | |
| 2009/0149680 A1 | 6/2009 | Wang et al. | |
| 2009/0224207 A1 | 9/2009 | Pham et al. | |
| 2009/0242832 A1 | 10/2009 | Pham et al. | |
| 2009/0278075 A1 | 11/2009 | Mahler et al. | |
| 2010/0029997 A1 | 2/2010 | Wang et al. | |
| 2010/0072415 A1 | 3/2010 | Rao et al. | |
| 2010/0076100 A1 | 3/2010 | Chen | |
| 2010/0090156 A1 | 4/2010 | Nappa et al. | |
| 2010/0112328 A1 | 5/2010 | Van Horn et al. | |
| 2010/0168482 A1 | 7/2010 | Rao et al. | |
| 2011/0155942 A1 | 6/2011 | Pigamo et al. | |
| 2012/0240477 A1 | 9/2012 | Nappa | |
| 2014/0191154 A1 | 7/2014 | Minor et al. | |
| 2017/0009117 A1 | 1/2017 | Mahler et al. | |
| 2017/0210960 A1 | 7/2017 | Deur-Bert et al. | |
| 2019/0194514 A1 | 6/2019 | Mahler et al. | |

FOREIGN PATENT DOCUMENTS

| | | |
|---|---|---|
| EP | 2 481 720 A2 | 8/2012 |
| EP | 2 634 165 B1 | 2/2020 |
| GB | 2 439 392 A | 12/2007 |
| GB | 2440258 A | 1/2008 |
| JP | 4-110388 A | 4/1992 |
| JP | H4-110388 A | 4/1992 |
| JP | 2011-508656 A | 1/2006 |
| JP | 2007-535611 A | 12/2007 |
| JP | 2009-514951 A | 4/2009 |
| JP | 2010-513517 A | 4/2010 |
| JP | 2010-531924 A | 9/2010 |
| JP | 2014-503494 A | 2/2014 |
| RU | 2073058 C1 | 2/1997 |
| WO | 2005/105947 A2 | 11/2005 |
| WO | 2006/069362 A2 | 6/2006 |
| WO | 2006/094303 A2 | 9/2006 |
| WO | 2007/002625 A2 | 1/2007 |
| WO | 2007/002703 A2 | 1/2007 |
| WO | 2007/053697 A2 | 5/2007 |
| WO | 2007/079431 A2 | 7/2007 |
| WO | 2007/086972 A2 | 8/2007 |
| WO | 2007/123786 A1 | 11/2007 |
| WO | 2007/148046 A1 | 12/2007 |
| WO | 2007/148046 A2 | 12/2007 |
| WO | 2008/002499 A2 | 1/2008 |
| WO | 2008/002500 A1 | 1/2008 |
| WO | 2008/009928 A2 | 1/2008 |
| WO | 2008/030439 A2 | 3/2008 |
| WO | 2008/054780 A2 | 5/2008 |
| WO | 2008/054781 A1 | 5/2008 |
| WO | 2008/054782 A1 | 5/2008 |
| WO | 2008/079265 A1 | 7/2008 |
| WO | 2008/121779 A1 | 10/2008 |
| WO | 2008/121785 A1 | 10/2008 |
| WO | 2008/121790 A1 | 10/2008 |
| WO | 2009/003084 A1 | 12/2008 |
| WO | 2009/003165 A1 | 12/2008 |
| WO | 2009/015317 A1 | 1/2009 |
| WO | 2009/018561 A2 | 2/2009 |
| WO | 2009/125201 A2 | 10/2009 |
| WO | 2009/137656 A1 | 11/2009 |
| WO | 2009/137658 A2 | 11/2009 |
| WO | 2010/056695 A2 | 5/2010 |
| WO | 2011/087825 A1 | 7/2011 |

OTHER PUBLICATIONS

Papadimitriou, Vassileios C., et al., $CF_3CF=CH_2$ and (Z)-$CF_3CF=CHF$: temperature dependent OH rate coefficients and global warming potentials, Physical Chemistry Chemical Physics, 2007, vol. 9, pp. 1-13.

(56) References Cited

OTHER PUBLICATIONS

Satterfield, C.N., Heterogeneous Catalysis in Industrial Practice, 2nd Edition, pp. 87-112, McGraw-Hill, New York (1991).
Heard, George L. et al., 1,2-FCl Rearrangement as an Intermediate Step in the Unimolecular 1,3-HCl Elimination from Chlorofluoropropanes, J. Phys. Chem. A, 201, pp. 1622-1625.
U.S. Appl. No. 11/588,464, filed Oct. 27, 2006 in the name of Honeywell International Inc. (Issued U.S. Pat. No. 7,560,602).
U.S. Appl. No. 61/126,810, filed May 7, 2008 in the name of E. I. du Pont de Nemours Company.
U.S. Appl. No. 61/085,141, filed Jul. 31, 2008 in the name of Honeywell International Inc.
U.S. Appl. No. 61/113,477, filed Nov. 11, 2008 in the name of Honeywell International Inc.
Opposition Brief submitted by Arkema France dated Nov. 16, 2018, against EP 2 271 725.
Opposition Brief submitted by Mexichem Fluor S.A. de C.V. dated Nov. 19, 2018, against EP 2 271 725.
Opposition Brief submitted by AGC Inc., dated Nov. 20, 2018, against EP 2 271 725.
Opposition Brief submitted by Daikin Industries, Ltd. Dated Nov. 21, 2018, against EP 2 271 725.
SynQuest Laboratories, Inc., Invoice No. B147-203 dated Aug. 13, 2007, billed to Arkema.
SynQuest Laboratories, Incorporated, Certificate of Analysis dated Aug. 8, 2007.
Exchanges of e-mails between Arkema and SynQuest dated Oct. 19, 2012-Oct. 31, 2012.
Technical report from Arkema.
First Declaration of Kazuhiro Takahashi submitted with Petition for Inter Partes Review of U.S. Pat. No. 8, 247,709, The Chemours Company FC, LLC.
Specifications for Fluorocarbon Refrigerants, 2006 Standard for Air-Conditioning & Refrigeration Institute, ARI Standard 700, 2006, pp. 1-15.
Calm, James M., ARTI Refrigerant Database, Sep. 1999, pp. 34-36, 168-170, 200-202, 267, 305-306, 336, 520-523 and 527.
Response to oral proceedings mailed Aug. 28, 2020 submitted by AGC Inc.
Response to oral proceedings mailed Aug. 31, 2020 submitted by Arkema.
Certificate of Analysis, SynQuest Laboratories, Incorporated, Product No. 1300-3-10, Analysis Date: Sep. 13, 2006.
Decision of Technical Board of Appeal dated Mar. 12, 2019 Application No. 09743642.2 (Appeal No. T2172/16).
Climate Change 2007, The Physical Science Basis, Working Group I Contribution to the Fourth Assessment Report of the Intergovernmental Panel on Climate Change, 2007, New York, New York.
1997 ASHRAE Handbook, Fundamentals, SI Edition, 1997, pp. 18.2-18.3, 18.10, Atlanta, GA.
ASHRAE Standard 34-2007, Designation and Safety Classification of Refrigerants, 2007, Atlanta GA.
Hughes, Michael H., Refrigeration Systems for HVAC, Refrigerants, Chapter 6.1.
Orkin et al., Rate Constants for the Reactions of OH with HFC-245cb (CH3CF2CF3) and Some Fluoroalkenes ($CH_2CHCF_3$, $CH_2CFCF_3$, $CF_2CFCF_3$, and $CF_2CF_2$). Journal of Physical Chemistry, 1997, pp. 9118-9124.
Written Demand submitted by AGC in Invalidation Trial for JP6435357B dated Sep. 18, 2020.
Written Demand submitted by AGC in Invalidation Trial for JP6585232B dated Sep. 18, 2020.
Nielsen, O.J., et al., Atmospheric chemistry of $CF_3CF=CH_2$: Kinetics and mechanisms of gas-phase reactions with Cl atoms, OH radicals, and $O_3$, ScienceDirect, Chemical Physics Letters, 2007, pp. 18-22, Morristown, NJ.
Climate Change 2007, The Physical Science Basis, Working Group I Contribution to the Fourth Assessment Report of the Intergovernmental Panel on Climate Change, Changes in Atmospheric Constituents and in Radiative Forcing, 2007, pp. 212.
Binary Article regarding Heat Sink (Heat Dissipation Plate) submitted as Exhibit A13 by AGC in Invalidation Trial to allege the meaning of heat sink.
Article regarding Heat Sink submitted as Exhibit A14 by AGC in Invalidation Trial to allege the meaning of heat sink.
Article submitted as Exhibit A15 by AGC in Invalidation Trial to allege the meaning of heat sink.

\* cited by examiner

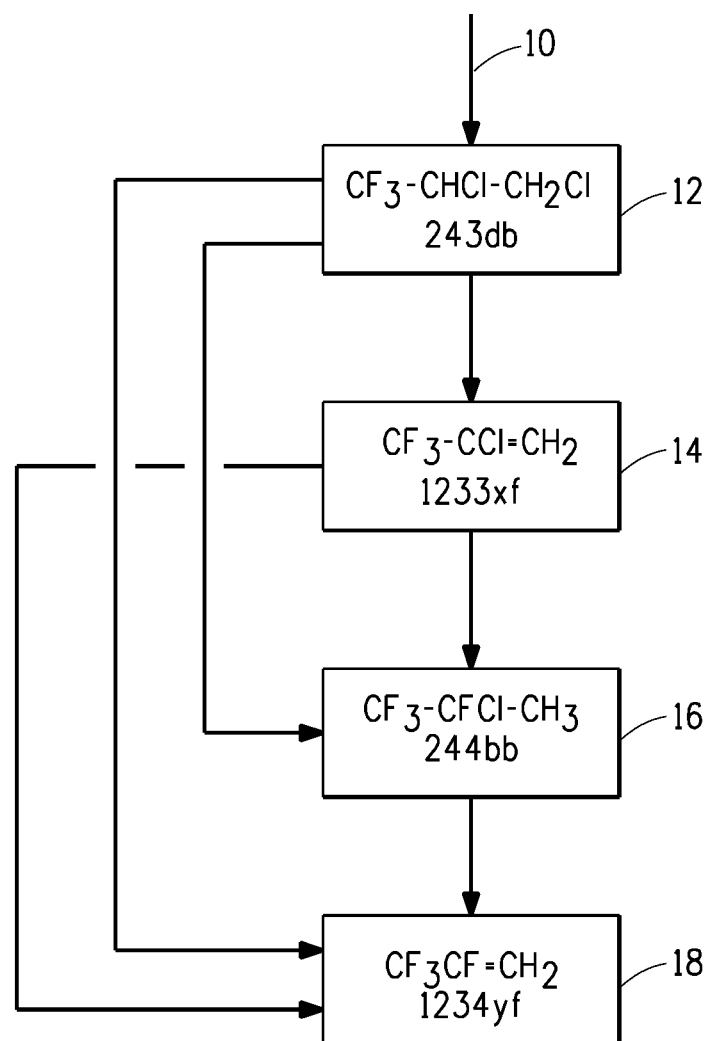

COMPOSITIONS COMPRISING 2,3-DICHLORO-1,1,1-TRIFLUOROPROPANE, 2-CHLORO-1,1,1-TRIFLUOROPROPENE, 2-CHLORO-1,1,1,2-TETRAFLUOROPROPANE OR 2,3,3,3-TETRAFLUOROPROPENE

BACKGROUND

Field of the Invention

The present disclosure relates to the field of compositions which may be useful as heat transfer compositions, aerosol propellants, foaming agents, blowing agents, solvents, cleaning agents, carrier fluids, displacement drying agents, buffing abrasion agents, polymerization media, expansion agents for polyolefins and polyurethane, gaseous dielectrics, extinguishing agents, and fire suppression agents in liquid or gaseous form. In particular, the present disclosure relates to compositions which may be useful as heat transfer compositions, such as 2,3,3,3,-tetrafluoropropene (HFO-1234yf, or 1234yf) or compositions comprising 2,3-dichloro-1,1,1-trifluoropropane (HCFC-243db or 243db), 2-chloro-1,1,1-trifluoropropene (HCFO-1233xf or 1233xf) or 2-chloro-1,1,1,2-tetrafluoropropane (HCFC-244bb).

2. Description of Related Art

New environmental regulations have led to the need for new compositions for use in refrigeration, air-conditioning and heat pump apparatus. Low global warming potential compounds are of particular interest.

SUMMARY OF THE INVENTION

Applicants have found that in preparing such new low global warming potential compounds, such as 1234yf, that certain additional compounds are present in small amounts.

Therefore, in accordance with the present invention, there is provided a composition comprising HFO-1234yf and at least one additional compound selected from the group consisting of HFO-1234ze, HFO-1243zf, HCFC-243db, HCFC-244db, HFC-245cb, HFC-245fa, HCFO-1233xf, HCFO-1233zd, HCFC-253fb, HCFC-234ab, HCFC-243fa, ethylene, HFC-23, CFC-13, HFC-143a, HFC-152a, HFO-1243zf, HFC-236fa, HCO-1130, HCO-1130a, HFO-1336, HCFC-133a, HCFC-254fb, HCFC-1131, HFC-1141, HCFO-1242zf, HCFO-1223xd, HCFC-233ab, HCFC-226ba, and HFC-227ca. The composition contains less than about 1 weight percent of the at least one additional compound.

Compositions comprising HCFC-243db, HCFO-1233xf, and/or to HCFC-244db are useful in processes to make HFO-1234yf. Therefore, compositions comprising 1234yf may contain some amount of HCFC-243db, HCFO-1233xf, and/or HCFC-244db, in addition to other compounds.

Therefore, in accordance with the present invention, there is provided a composition comprising HCFC-243db and at least one additional compound selected from the group consisting of ethylene, HFC-23, CFC-13, HFC-143a, HFC-152a, HFO-1234yf, HFO-1243zf, HFC-236fa, HCO-1130, HCO-1130a, HFO-1234ze, HFO-1336, HCFC-244bb, HCFC-244db, HFC-245fa, HFC-245cb, HCFC-133a, HCFC-254fb, HCFC-1131, HCFO-1233xf, HCFO-1233zd, HCFO-1242zf, HCFC-253fb, HCFO-1223xd, HCFC-233ab, HCFC-226ba, and HFC-227ca. The composition may contain anywhere from greater than zero weight percent to about 99 weight percent of HCFC-243db.

In addition, in accordance with the present invention, there is further provided a composition comprising HCFO-1233xf and at least one additional compound selected from the group consisting of HCFO-1233zd, HCFO-1232xd, HCFO-1223xd, HCFC-253fb, HCFC-233ab, HFO-1234yf, HFO-1234ze, ethylene, HFC-23, CFC-13, HFC-143a, HFC-152a, HFO-1243zf, HFC-236fa, HCO-1130, HCO-1130a, HFO-1336, HCFC-244bb, HCFC-244db, HFC-245fa, HFC-245cb, HCFC-133a, HCFC-254fb, HCFC-1131, HCFO-1242zf, HCFO-1223xd, HCFC-233ab, HCFC-226ba, and HFC-227ca. The composition may contain anywhere from greater than zero weight percent to about 99 weight percent of HCFO-1233xf.

In addition, in accordance with the present invention, there is also provided a composition comprising HCFC-244bb and at least one additional compound selected from the group consisting of HCFO-1233zd, HCFO-1232xd, HCFO-1223xd, HCFC-253fb, HCFC-233ab, HFO-1234yf, HFO-1234ze, ethylene, HFC-23, CFC-13, HFC-143a, HFC-152a, HFO-1243zf, HFC-236fa, HCO-1130, HCO-1130a, HFO-1336, HCFC-244db, HFC-245fa, HFC-245cb, HFC-245eb, HCFC-133a, HCFC-254fb, HCFC-1131, HCFO-1242zf, HCFO-1223xd, HCFC-233ab, HCFC-226ba, and HFC-227ca. The composition may contain anywhere from greater than zero weight percent to about 99 weight percent of HCFC-244bb.

BRIEF DESCRIPTION OF THE DRAWINGS

FIG. 1 is a schematic drawing showing a reaction for producing HFO-1234yf from 243db.

DETAILED DESCRIPTION OF THE PREFERRED EMBODIMENTS

HFO-1234yf has been suggested for use as a refrigerant, heat transfer fluid, aerosol propellant, foam expansion agent, among other uses. It has also, advantageously, been found that HFO-1234yf has a low global warming potential (GWP) as reported by V. C. Papadimitriou, et al. in Physical Chemistry Chemical Physics, 2007, volume 9, pages 1-13. Thus, HFO-1234yf is a good candidate for replacing the higher GWP saturated HFC refrigerants.

In one embodiment, the present disclosure provides a composition comprising HFO-1234yf and at least one additional compound selected from the group consisting of HFO-1234ze, HFO-1243zf, HCFC-243db, HCFC-244db, HFC-245cb, HFC-245fa, HCFO-1233xf, HCFO-1233zd, HCFC-253fb, HCFC-234ab, HCFC-243fa, ethylene, HFC-23, CFC-13, HFC-143a, HFC-152a, HFC-236fa, HCO-1130, HCO-1130a, HFO-1336, HCFC-133a, HCFC-254fb, HCFC-1131, HFO-1141, HCFO-1242zf, HCFO-1223xd, HCFC-233ab, HCFC-226ba, HFC-227ca.

In one embodiment, the total amount of additional compound(s) in the composition comprising HFO-1234yf ranges from greater than zero weight percent to less than 1 weight percent.

In some embodiments, the impurities present in the HCFC-243db, HCFO-1233xf, and HCFC-244bb will remain intact during the reaction to make HFO-1234yf, thus they are included in the additional compounds.

In another embodiment, the present disclosure provides a composition comprising HCFC-243db and at least one additional compound selected from the group consisting of ethylene, HFC-23, CFC-13, HFC-143a, HFC-152a, HFO-1234yf, HFO-1243zf, HFC-236fa, HCO-1130, HCO-1130a, HFO-1234ze, HFO-1336, HCFC-244bb, HCFC-244db, HFC-245fa, HFC-245cb, HCFC-133a, HCFC-254fb, HCFC-1131, HCFO-1233xf, HCFO-1233zd, HCFO-1242zf, HCFC-253fb, HCFO-1223xd, HCFC-233ab, HCFC-226ba, and HFC-227ca.

In one embodiment, the total amount of additional compound(s) in the composition comprising HCFC-243db ranges from greater than zero weight percent to about 99 weight percent. In another embodiment, the total amount of additional compounds ranges from about 1 weight percent to about 80 weight percent. In another embodiment, the total amount of additional compound(s) ranges from about 1 weight percent to about 50 weight percent. In another embodiment, the total amount of additional compound(s) ranges from about 1 weight percent to about 30 weight percent. In another embodiment, the total amount of additional compound(s) ranges from about 1 weight percent to about 10 weight percent.

In some embodiments, certain precursor compounds to HCFC-243db contain impurities that appear in the HCFC-243db. In other embodiments, the additional compounds are formed by reaction of these precursor impurities. In other embodiments, the reaction conditions under which the HCFC-243db is produced also produce by-products, by which is meant alternative reaction pathways may produce additional compounds depending upon the particular conditions under which the HCFC-243db is produced.

In another embodiment, the present disclosure provides a composition comprising HCFO-1233xf and at least one additional compound selected from the group consisting of HCFO-1233zd, HCFO-1232xd, HCFO-1223xd, HCFC-253fb, HCFC-233ab, HFO-1234yf, HFO-1234ze, ethylene, HFC-23, CFC-13, HFC-143a, HFC-152a, HFO-1243zf, HFC-236fa, HCO-1130, HCO-1130a, HFO-1336, HCFC-244bb, HCFC-244db, HFC-245fa, HFC-245cb, HCFC-133a, HCFC-254fb, HCFC-1131, HCFO-1242zf, HCFO-1223xd, HCFC-233ab, HCFC-226ba, HFC-227ca.

In one embodiment, the total amount of additional compound(s) in the composition comprising HCFO-1233xf ranges from greater than zero weight percent to about 99 weight percent. In another embodiment, the total amount of additional compounds ranges from about 1 weight percent to about 80 weight percent. In another embodiment, the total amount of additional compound(s) ranges from about 1 weight percent to about 50 weight percent. In another embodiment, the total amount of additional compound(s) ranges from about 1 weight percent to about 30 weight percent. In another embodiment, the total amount of additional compound(s) ranges from about 1 weight percent to about 10 weight percent.

In some embodiments, certain precursor compounds to HCFO-1233xf contain impurities that appear in the HCFO-1233xf. In other embodiments, the additional compounds are formed by reaction of these precursor impurities. In other embodiments, the reaction conditions under which the HCFO-1233xf is produced also produce by-products, by which is meant alternative reaction pathways may produce additional compounds depending upon the particular conditions under which the HCFO-1233xf is produced.

In another embodiment, the present disclosure provides a composition comprising HCFC-244bb and at least one additional compound selected from the group consisting of HCFO-1233zd, HCFO-1232xd, HCFO-1223xd, HCFC-253fb, HCFC-233ab, HFO-1234yf, HFO-1234ze, ethylene, HFC-23, CFC-13, HFC-143a, HFC-152a, HFO-1243zf, HFC-236fa, HCO-1130, HCO-1130a, HFO-1336, HCFC-244db, HFC-245fa, HFC-245cb, HFC-245eb, HCFC-133a, HCFC-254fb, HCFC-1131, HCFO-1242zf, HCFO-1223xd, HCFC-233ab, HCFC-226ba, HFC-227ca.

In one embodiment, the total amount of additional compound(s) in the composition comprising HCFC-244bb ranges from greater than zero weight percent to about 99 weight percent. In another embodiment, the total amount of additional compounds ranges from about 1 weight percent to about 80 weight percent. In another embodiment, the total amount of additional compound(s) ranges from about 1 weight percent to about 50 weight percent. In another embodiment, the total amount of additional compound(s) ranges from about 1 weight percent to about 30 weight percent. In another embodiment, the total amount of additional compound(s) ranges from about 1 weight percent to about 10 weight percent.

In some embodiments, certain precursor compounds to HCFC-244bb contain impurities that appear in the HCFC-244bb. In other embodiments, the additional compounds are formed by reaction of these precursor impurities. In other embodiments, the reaction conditions under which the HCFC-244bb is produced also produce by-products that then appear in the HCFC-243db compositions, by which is meant alternative reaction pathways may produce additional compounds depending upon the particular conditions under which the HCFC-244bb is produced.

The compositions disclosed herein comprising HFO-1234yf are useful as low global warming potential (GWP) heat transfer compositions, aerosol propellant, foaming agents, blowing agents, solvents, cleaning agents, carrier fluids, displacement drying agents, buffing abrasion agents, polymerization media, expansion agents for polyolefins and polyurethane, gaseous dielectrics, extinguishing agents, and fire suppression agents in liquid or gaseous form. The disclosed compositions can act as a working fluid used to carry heat from a heat source to a heat sink. Such heat transfer compositions may also be useful as a refrigerant in a cycle wherein the fluid undergoes a phase change; that is, from a liquid to a gas and back or vice versa.

Examples of heat transfer systems include but are not limited to air conditioners, freezers, refrigerators, heat pumps, water chillers, flooded evaporator chillers, direct expansion chillers, walk-in coolers, heat pumps, mobile refrigerators, mobile air conditioning units and combinations thereof.

As used herein, mobile refrigeration apparatus, mobile air conditioning or mobile heating apparatus refers to any refrigeration, air conditioner, or heating apparatus incorporated into a transportation unit for the road, rail, sea or air. In addition, mobile refrigeration or air conditioner units, include those apparatus that are independent of any moving carrier and are known as "intermodal" systems. Such intermodal systems include "containers' (combined sea/land transport) as well as "swap bodies" (combined road/rail transport).

As used herein, stationary heat transfer systems are systems associated within or attached to buildings of any variety. These stationary applications may be stationary air conditioning and heat pumps (including but not limited to chillers, high temperature heat pumps, residential, commercial or industrial air conditioning systems, and including window, ductless, ducted, packaged terminal, chillers, and those exterior but connected to the building such as rooftop systems). In stationary refrigeration applications, the disclosed compositions may be useful in equipment including commercial, industrial or residential refrigerators and freezers, ice machines, self-contained coolers and freezers, flooded evaporator chillers, direct expansion chillers, walk-in and reach-in coolers and freezers, and combination systems. In some embodiments, the disclosed compositions may be used in supermarket refrigerator systems.

The compounds making up the disclosed compositions are defined in Table 1.

TABLE 1

| Code | Structure | Chemical name |
|---|---|---|
| | $CH_2=CH_2$ | Ethylene |
| CFC-13 | $CF_3Cl$ | chlorotrifluoromethane |
| HFC-23 | $CHF_3$ | trifluoromethane |
| HCFC-133a | $CF_3CH_2Cl$ | 2-chloro-1,1,1-trifluoroethane |
| HFO-134 | $CHF_2CHF_2$ | 1,1,2,2-tetrafluoroethane |
| HFO-134a | $CF_3CH_2F$ | 1,1,1,2-tetrafluoroethane |
| HFC-143a | $CF_3CH_3$ | 1,1,1-trifluoroethane |
| HFC-152a | $CHF_2CH_3$ | 1,1-difluoroethane |
| HFC-227ca | $CF_3CF_2CHF_2$ | 1,1,1,2,2,3,3-heptafluoropropane |
| HCFC-233ab | $CF_3CCl_2CH_2Cl$ | 1,2,2-trichloro-3,3,3-trifluoropropane |
| HCFC-234ab | $CF_3CCl_2CH_2F$ | 2,2-dichloro-1,1,1,3-tetrafluoropropane |
| HFC-236fa | $CF_3CH_2CF_3$ | 1,1,1,3,3,3-hexafluoropropane |
| HCFC-243fa | $CF_3CH_2CHCl_2$ | 3,3-dichloro-1,1,1-trifluoropropane |
| HCFC-243db | $CF_3CHClCH_2Cl$ | 2,3-dichloro-1,1,1-trifluoropropane |
| HCFC-244bb | $CF_3CFClCH_3$ | 2-chloro-1,1,1,2-tetrafluoropropane |
| HCFC-244db | $CF_3CHClCH_2F$ | 2-chloro-1,1,1,3-tetrafluoropropane |
| HFC-245fa | $CF_3CH_2CHF_2$ | 1,1,1,3,3-pentafluoropropane |
| HFC-245cb | $CF_3CF_2CH_3$ | 1,1,1,2,2-pentafluoropropane |
| HFC-245eb | $CF_3CHFCH_2F$ | 1,1,1,2,3-pentafluoropropane |
| HCFC-253fb | $CF_3CH_2CH_2Cl$ | 3-chloro-1,1,1-trifluoropropane |
| HFC-254fb | $CF_3CH_2CH_2F$ | 1,1,1,3-tetrafluoropropane |
| HCO-1130 | $CHCl=CHCl$ | E- and/or Z-1,2-dichloroethene |
| HCO-1130a | $CCl_2=CH_2$ | 1,1-dichloroethene |
| HCFC-1131 | $CHF=CHCl$ | E- and/or Z-1-chloro-2-fluoroethene |
| HFO-1141 | $CHF=CH_2$ | fluoroethene |
| HCFO-1223xd | $CF_3CCl=CHCl$ | 1,2-difluoro-3,3,3-trifluoropropene |
| HCFO-1233zd | $CF_3CH=CHCl$ | E- and/or Z-1-chloro-3,3,3-trifluoropropene |
| HCFO-1233xf | $CF_3CCl=CH_2$ | 2-chloro-1,1,1-trifluoropropene |
| HFO-1234yf | $CF_3CF=CH_2$ | 2,3,3,3-tetrafluoropropene |
| HFO-1234ze | $CF_3CH=CHF$ | E- and/or Z-1,3,3,3-tetrafluoropropene |
| HCFO-1242zf | $CClF_2CH=CH_2$ | 3-chloro-3,3-difluoropropene |
| HFO-1243zf | $CF_3CH=CH_2$ | 1,1,1-trifluoropropene (TFP) |
| HFO-1336 | $C_4H_2F_6$ | E- and/or Z-hexafluorobutene |

HCFC-243db, HCFO-1233xf, and HCFC-244bb are available from specialty chemical manufacturers, including SynQuest Laboratories, Inc. (Alachua, Fla., U.S.A.) or may be made as described herein. For instance, HCFC-243db, HCFO-1233xf, and HCFC-244bb may be prepared by non-catalytic chlorination of HFO-1243zf, as described in International Patent Application Publication No. WO2008/054782, published May 8, 2008. Also, HCFO-1233xf and HCFC-244bb may be prepared by catalytic fluorination of 243db as described in International Patent Application Publication No. WO2008/054781, published May 8, 2008. The additional compounds present in each disclosed composition will depend upon the method of manufacture.

In some embodiments, certain precursor compounds to HCFC-243db, HCFO-1233xf, or HCFC-244bb contain impurities that then appear as additional compounds in the described compositions. In other embodiments, these precursor compounds may themselves react during the 243db formation to form additional compounds that then appear in the HCFC-243db compositions. In other embodiments, the reaction conditions under which the HCFC-243db, HCFO-1233xf, or HCFC-244bb are produced also produce by-products, by which is meant adventitious reaction pathways may occur simultaneously to produce compounds other than HCFC-243db, HCFO-1233xf or HCFC-244bb and the quantity and identity of these additional compounds will depend upon the particular conditions under which the HCFC-243db, HCFO-1233xf or HCFC-244bb are produced.

In one embodiment, HFO-1234yf may be produced in a single step from HCFC-243db. In another embodiment, the reaction sequence may be carried out in a step-wise manner. In another embodiment, HCFO-1233xf may be produced from HCFC-243db and then HCFO-1233xf may be converted directly to HFO-1234yf. In yet another embodiment, HCFC-244bb may be produced from HCFC-243db and then the HCFC-244bb may be converted to HFO-1234yf.

Fluorochlorination of HFO-1243zf

In some embodiments, HFO-1243zf may be used to make HCFC-243db, HCFO-1233xf, HCFC-244db, and/or HFO-1234yf by fluorochlorination. HFO-1243zf is commercially available from E.I. DuPont de Nemours and Company (Wilmington, Del., USA).

The fluorochlorination reaction may be carried out in the liquid or vapor phase. For liquid phase embodiments of the invention, the reaction of HFO-1243zf with HF and $Cl_2$ may be conducted in a liquid-phase reactor operating in batch, semi-batch, semi-continuous, or continuous modes. In the batch mode, HFO-1243zf, $Cl_2$, and HF are combined in an autoclave or other suitable reaction vessel and heated to the desired temperature.

In one embodiment, this reaction is carried out in semi-batch mode by feeding $Cl_2$ to a liquid-phase reactor containing HF and HFO-1243zf or by feeding HFO-1243zf and $Cl_2$ to a liquid-phase reactor containing HF, or by feeding $Cl_2$ to a mixture containing HF and reaction products formed by initially heating HFO-1243zf and HF. In another embodiment, HF and $Cl_2$ may be fed to a liquid-phase reactor containing a mixture of HFO-1243zf and reaction products formed by reacting HF, $Cl_2$, and HFO-1243zf. In another embodiment of the liquid-phase process, HF, $Cl_2$, and HFO-1243zf may be fed concurrently in the desired stoichiometric ratio to the reactor containing a mixture of HF and reaction products formed by reacting HF, $Cl_2$, and HFO-1243zf.

Suitable temperatures for the reaction of HF and $Cl_2$ with HFO-1243zf in the liquid-phase reactor are, in one embodiment, from about 80° C. to about 180° C., and in another embodiment, from about 100° C. to about 150° C. Higher temperatures typically result in greater conversion of the HFO-1243zf.

A suitable molar ratio of HF to total amount of HFO-1243zf fed to the liquid-phase reactor is, in one embodiment, at least stoichiometric and in another embodiment, is from about 5:1 to about 100:1. Of note are embodiments wherein the molar ratio of HF to HFO-1243zf is from about 8:1 to about 50:1. A suitable molar ratio of $Cl_2$ to total amount of HFO-1243zf fed to the liquid-phase reactor is from about 1:1 to about 2:1.

The reactor pressure in the liquid-phase process is not critical and in batch reactions is usually the autogenous pressure of the system at the reaction temperature. The pressure of the system increases as hydrogen chloride is formed by replacement of hydrogen substituents by chlorine, and by replacement of chlorine substituents by fluorine in the starting materials and intermediate reaction products. In a continuous process it is possible to set the pressure of the reactor in such a way that the lower boiling products of the reaction, such as HCl, HFO-1234yf ($CF_3CF=CH_2$), E/Z-1234ze (E/Z-$CF_3CH=CHF$), and HFC-245cb ($CF_3CF_2CH_3$), are vented from the reactor, optionally through a packed column or condenser. In this manner, higher boiling intermediates remain in the reactor and the volatile products are removed. Typical reactor pressures are from about 20 psig (239 kPa) to about 1,000 psig (6,994 kPa).

In some embodiments, in which the reaction is conducted using a liquid-phase process, catalysts which may be used include carbon, $AlF_3$, $BF_3$, $FeCl_{3-a}F_a$ (where a=0 to 3), $FeX_3$ supported on carbon, $SbCl_{3-a}F_a$, $AsF_3$, $MCl_{5-b}F_b$ (where b=0 to 5 and M=Sb, Nb, Ta, or Mo), and $M'Cl_{4-c}F_c$ (where c=0 to 4, and M'=Sn, Ti, Zr, or Hf). In another embodiment, catalysts for the liquid phase process are $MCl_{5-b}F_b$ (where b=0 to 5 and M=Sb, Nb, or Ta).

In another embodiment, the reaction of HF and $Cl_2$ with HFO-1243zf is carried out in the vapor phase. Typically a heated reactor is used. A number of reactor configurations are possible including horizontal or vertical orientation of the reactor as well as the sequence of reaction of the HFO-1243zf with HF and $Cl_2$. In one embodiment of the invention, the HFO-1243zf may be initially vaporized and fed to the reactor as a gas.

In another embodiment of the invention, HFO-1243zf may be contacted with HF, optionally in the presence of $Cl_2$, in a pre-reactor prior to reaction in the vapor-phase reactor. In one embodiment, the pre-reactor may be empty. In another embodiment, the reactor is filled with a suitable packing such as nickel-copper alloys commercially available from Special Metals Corp. (New Hartford, N.Y.) under the trademark Monel®, (hereinafter "Monel®") nickel-based alloys commercially available from Haynes International (Kokomo, Ind.) under the trademark Hastelloy®, (hereinafter "Hastelloy®") or other nickel alloy turnings or wool, or other material inert to HCl and HF which allows efficient mixing of HFO-1243zf and HF vapor.

Suitable temperatures for the pre-reactor in one embodiment are from about 80° C. to about 250° C., in another embodiment, from about 100° C. to about 200° C. Temperatures greater than about 100° C. result in some conversion of the HFO-1243zf to compounds having a higher degree of fluorination. Higher temperatures result in greater conversion of the HFO-1243zf entering the reactor and a greater degree of fluorination in the converted compounds. Under these conditions, for example, a mixture of HF, $Cl_2$, and HFO-1243zf is converted to a mixture containing predominantly HCFC-243db and HCFC-244db ($CF_3CHClCH_2F$).

The degree of fluorination reflects the number of fluorine substituents that replace chlorine substituents in the HFO-1243zf and their chlorinated products. For example, HCFC-253fb represents a higher degree of fluorination than HCC-250fb and HFO-1243zf represents a higher degree of fluorination than HCO-1240zf.

The molar ratio of HF to the total amount of HFO-1243zf in the pre-reactor is in one embodiment, from about the stoichiometric ratio of HF to the total amount of HFO-1243zf to about 50:1. In another embodiment, the molar ratio of HF to the total amount of HFO-1243zf in the pre-reactor is from about twice the stoichiometric ratio of HF to the total amount of HFO-1243zf to about 30:1. In another embodiment, the molar ratio of HF to the total amount of HFO-1243zf is present in the pre-reactor, and no additional amount of HF is added to the vapor-phase reaction zone.

In another embodiment, the HFO-1243zf may be contacted with $Cl_2$ in a pre-reactor, optionally in the presence of HF, prior to reaction in the vapor-phase reactor.

Suitable temperatures for the pre-reactor for this embodiment of the invention are from about 80° C. to about 250° C., preferably from about 100° C. to about 200° C. Under these conditions, at least a portion of HFO-1243zf is converted to HCFC-243db. Higher temperatures typically result in a higher degree of halogenation of the HFO-1243zf.

The degree of halogenation reflects the total number of halogen substituents (chlorine plus fluorine) in a halopropane and/or halopropene product. For example, HFO-1234yf has a higher degree of halogenation (i.e., 4) than does HFO-1243zf (i.e., 3).

The molar ratio of $Cl_2$ to the total amount of HFO-1243zf is, in one embodiment, from about 0.5:1 to about 2:1. In another embodiment, the molar ratio of $Cl_2$ to the total amount of the HFO-1243zf is from about 1.1:1 to about 1:1.

In one embodiment, the HFO-1243zf is vaporized, optionally in the presence of HF, and fed to a pre-reactor or to a vapor-phase reactor along with HF and $Cl_2$.

Suitable temperatures for the vapor-phase reaction are from about 120° C. to about 500° C. Temperatures of from about 250° C. to about 350° C. favor the formation of HFO-1234yf and HFC-245cb. Temperatures of from about 350° C. to about 450° C. favor the formation of HFO-1234ze, HFC-245fa, and HCFO-1233zd. At temperatures of from about 250° C. to about 450° C., some HCFO-1233xf is also produced. Higher temperatures result in greater conversion of HFO-1243zf and higher degrees of fluorination and halogenation in the converted compounds.

Suitable reactor pressures for the vapor-phase reactor may be from about 1 to about 30 atmospheres. A pressure of about 15 to about 25 atmospheres may be advantageously employed to facilitate separation of HCl from other reaction products, and the suitable reaction time may vary from about 1 to about 120 seconds, preferably from about 5 to about 60 seconds.

The molar ratio of HF to the total amount of HFO-1243zf for the vapor-phase reaction is, in one embodiment, from about the stoichiometric ratio of HF to the total amount of HFO-1243zf to about 50:1 and, in another embodiment, from about 10:1 to about 30:1.

In one embodiment, a catalyst is used in the reaction zone for the vapor-phase reaction of HF and $Cl_2$ with HFO-1243zf. Chlorofluorination catalysts which may be used in the vapor phase reaction include carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals (including elemental metals, metal oxides, metal halides, and/or other metal salts); metals supported on aluminum fluoride; metals supported on fluorided alumina; metals supported on alumina; and metals supported on carbon; mixtures of metals.

Suitable metals for use as catalysts (optionally supported on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). In one embodiment, when used on a support, the total metal content of the catalyst will be from about 0.1 to about 20 percent by weight based on the total weight of the catalyst; in another embodiment from about 0.1 to about 10 percent by weight based on the total weight of the catalyst.

Suitable chlorofluorination catalysts for the vapor-phase reactions include chromium-containing catalysts including chromium(III) oxide ($Cr_2O_3$); $Cr_2O_3$ with other metals such as magnesium halides or zinc halides supported on $Cr_2O_3$; chromium(III) halides supported on carbon; mixtures of chromium and magnesium (including elemental metals, metal oxides, metal halides, and/or other metal salts) optionally supported on graphite; and mixtures of chromium and other metals (including elemental metals, metal oxides, metal halides, and/or other metal salts) optionally supported on graphite, alumina, or aluminum halides such as aluminum fluoride.

Chromium-containing catalysts are well known in the art. They may be prepared by either precipitation methods or impregnation methods as generally described by Satterfield on pages 87-112 in *Heterogeneous Catalysis in Industrial Practice*, $2^{nd}$ edition (McGraw-Hill, New York, 1991).

Of note are chlorofluorination catalysts that comprise at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms, and crystalline alpha-chromium oxide where from about 0.05 atom % to about 6 atom % of the chromium atoms in the alpha-chromium oxide lattice are replaced by trivalent cobalt atoms which has been treated with a fluorinating agent. These catalysts, including their preparation, have been disclosed in U.S. Patent Application Publication US2005/0228202.

Optionally, the metal-containing catalysts described above can be pretreated with HF. This pretreatment can be accomplished, for example, by placing the metal-containing catalyst in a suitable container, and thereafter, passing HF over the metal-containing catalyst. In one embodiment, such container can be the reactor used to perform the chlorofluorination reaction. In one embodiment, the pretreatment time is from about 15 to about 300 minutes, and the pretreatment temperature is from about 200° C. to about 450° C.

In one embodiment, the product mixture comprises HFC-245cb, HFC-245fa, HFO-1234yf, HFO-1234ze, HCFO-1233zd and HCFO-1233xf.

In one embodiment, halopropane by-products that may be formed in the chlorofluorination reactions having higher degrees of halogenation and/or fluorination than pentafluoropropanes include $CF_3CCl_2CF_3$ (CFC-216aa), $CF_3CClFCClF_2$ (CFC-216ba), $CF_3CClFCF_3$ (CFC-217ba), $CF_3CF_2CClF_2$ (CFC-217ca), $CF_3CHFCF_3$(HFC-227ea), $CF_3CF_2CHF_2$ (HFC-227ca), $CF_3CClFCHF_2$ (HCFC-226ba), $CF_3CF_2CHClF$ (HCFC-226ca), $CF_3CHClCF_3$ (HCFC-226da), $CF_3CCl_2CHF_2$ (HCFC-225aa), $CF_3CClFCHClF$ (HCFC-225ba), $CF_3CF_2CHCl_2$ (HCFC-225ca), $CF_3CCl_2CClF_2$ (CFC-215aa), $CF_3CClFCCl_2F$ (CFC-215bb), $CF_3CCl_2CCl_2F$ (HCFC-214ab), $CF_3CCl_2CHClF$ (HCFC-224aa), and $CF_3CClFCHCl_2$ (HCFC-224ba).

In one embodiment, halopropene by-products that may be formed in the chlorofluorination reactions having a higher degree of halogenation than tetrafluoropropenes include $CF_3CCl$=$CHCl$ (HCFO-1223xd).

In one embodiment, the product comprises HCFC-243db and at least one additional compound selected from the group consisting of ethylene, HFC-23, CFC-13, HFC-143a, HFC-152a, HFO-1234yf, HFO-1243zf, HFC-236fa, HCO-1130, HCO-1130a, HFO-1234ze, HFO-1336, HCFC-244db, HFC-245fa, HFC-245cb, HCFC-133a, HCFC-254fb, HCFC-1131, HCFO-1233xf, HCFO-1233zd, HCFO-1242zf, HCFC-253fb, HCFO-1223xd, HCFC-233ab, HCFC-226ba, and HFC-227ca.

In cases where the product mixture produced by the processes of this invention comprises (i) product compounds HFC-245cb, HFC-245fa, HFO-1234yf, HFO-1234ze, HCFO-1233zd and HCFO-1233xf, (ii) HF, HCl, and $Cl_2$, (iii) higher boiling by-products such as $CF_3CHClCH_2Cl$ (HCFC-243db), $CF_3CHClCH_2F$ (HCFC-244bb) and (iv) chlorinated by-products such as $C_3HCl_3F_4$, $C_3HCl_2F_5$, $C_3HClF_6$, $C_3Cl_3F_5$, and $C_3Cl_2F_6$, the separation processes, such as distillation, may be employed to recover the product compounds from such a product mixture.

Fluorination of HCFC-243db

In some embodiments, HCFC-243db may be used to make HCFC-HCFO-1233xf, HCFC-244db, and/or HFO-1234yf by fluorination. These reactions are shown in FIG. 1. The fluorination reaction may be carried out in the liquid or vapor phase. For liquid phase embodiments of the invention, the reaction of HCFC-243db with HF may be conducted in a liquid-phase reactor operating in batch, semi-batch, semi-continuous, or continuous modes. In the batch mode, starting HCFC-243db and HF are combined in an autoclave or other suitable reaction vessel and heated to the desired temperature.

In one embodiment, this reaction is carried out in semi-batch mode by feeding HF to a liquid-phase reactor containing HCFC-243db or by feeding HCFC-243db to a liquid-phase reactor containing HF, or by feeding HF to a mixture containing HF and reaction products formed by initially heating HCFC-243db and HF. In another embodiment, HF may be fed to a liquid-phase reactor containing a mixture of HCFC-243db and reaction products formed by the reaction of HF, and HCFC-243db. In another embodiment of the liquid-phase process, HF, and HCFC-243db may be fed concurrently in the desired stoichiometric ratio to the reactor containing a mixture of HF and reaction products formed by reacting HF, and HCFC-243db.

Suitable temperatures for the reaction of HF with HCFC-243db in the liquid-phase reactor are, in one embodiment, from about 80° C. to about 180° C., in another embodiment, from about 100° C. to about 150° C. Higher temperatures typically result in greater conversion of the HCFC-243db.

A suitable molar ratio of HF to HCFC-243db fed to the liquid-phase reactor is, in one embodiment, at least stoichiometric and, in another embodiment, is from about 5:1 to about 100:1. Of note are embodiments wherein the molar ratio of HF to HCFC-243db is from about 8:1 to about 50:1.

The reactor pressure in the liquid-phase process is not critical and in batch reactions is usually the autogenous pressure of the system at the reaction temperature. The pressure of the system increases as hydrogen chloride is formed by replacement of chlorine substituents by fluorine in the HCFC-243db and intermediate reaction products. In a continuous process it is possible to set the pressure of the reactor in such a way that the lower boiling products of the reaction, such as HCl, $CF_3CF$=$CH_2$, and E/Z-$CF_3CH$=$CHF$, are vented from the reactor, optionally through a packed column or condenser. In this manner, higher boiling intermediates remain in the reactor and the volatile products are removed. Typical reactor pressures are from about 20 psig (239 kPa) to about 1,000 psig (6,994 kPa).

In embodiments in which the reaction is conducted using a liquid-phase process, catalysts which may be used include carbon, $AlF_3$, $BF_3$, $FeCl_{3-a}F_a$ (where a=0 to 3), $FeX_3$ supported on carbon, $SbCl_{3-a}F_a$, $AsF_3$, $MCl_{5-b}F_b$ (where b=0 to 5 and M=Sb, Nb, Ta, or Mo), and $M'Cl_{4-c}F_c$ (where c=0 to 4, and M'=Sn, Ti, Zr, or Hf). In one embodiment, catalysts for the liquid phase process are $MCl_{5-b}F_b$ (where b=0 to 5 and M=Sb, Nb, or Ta).

In one embodiment, the reaction of HF with HCFC-243db is carried out in the vapor phase. Typically a heated reactor is used. A number of reactor configurations are possible including horizontal or vertical orientation of the reactor as well as the sequence of reaction of the starting materials with HF. In one embodiment, the HCFC-243db may be initially vaporized and fed to the reactor as a gas.

In another embodiment of the invention, the HCFC-243db may be contacted with HF in a pre-reactor prior to reaction in the vapor-phase reactor. The pre-reactor may be empty, but is preferably filled with a suitable packing such as nickel-copper alloys commercially available from Special Metals Corp. (New Hartford, N.Y.) under the trademark Monel®, nickel-based alloys such as Hastelloy®, or other nickel alloy turnings or wool, or other material inert to HCl and HF which allows efficient mixing of HCFC-243db and HF vapor.

Suitable temperatures for the pre-reactor in one embodiment are from about 80° C. to about 250° C., in another embodiment, from about 100° C. to about 200° C. Temperatures greater than about 100° C. result in some conversion of the HCFC-243db to compounds having a higher degree of fluorination. Higher temperatures result in greater conversion of the HCFC-243db entering the reactor and a greater degree of fluorination in the converted compounds. Under these conditions, for example, a mixture of HF and HCFC-243db is converted to a mixture containing predominantly HF, HCl, HCFC-243db, HCFC-244db ($CF_3CHClCH_2F$), and HCFO-1233xf.

The degree of fluorination reflects the number of fluorine substituents that replace chlorine substituents in the HCFC-243db and their fluorinated products. For example, HFO-1234yf represents a higher degree of fluorination than HCFO-1233xf.

The molar ratio of HF to the total amount of HCFC-243db in the pre-reactor is, in one embodiment, from about the stoichiometric ratio of HF to the total amount of HCFC-243db to about 50:1. In another embodiment, the molar ratio of HF to the total amount of HCFC-243db in the pre-reactor is from about twice the stoichiometric ratio of HF to the total amount of HCFC-243db to about 30:1. In another embodiment, the molar ratio of HF to the amount of HCFC-243db is present in the pre-reactor, and no additional amount of HF is added to the vapor-phase reaction zone.

In one embodiment, the HCFC-243db and HF are vaporized and fed to a pre-reactor or to a vapor-phase reactor.

Suitable temperatures for the vapor-phase reaction are from about 120° C. to about 500° C. Temperatures in the range of from about 300° C. to about 350° C. favor the formation of HFO-1234yf and HFC-245cb and HCFO-1233xf. Temperatures in the range of from about 350° C. to about 450° C. favor the additional formation of HFO-1234ze, HFC-245fa, and HCFO-1233zd. Higher temperatures result in greater conversion of HCFC-243db and greater degrees of fluorination in the converted products. Reactor temperatures of from about 150° C. to about 275° C. favor the formation of HCFO-1233xf as the major product.

Suitable reactor pressures for the vapor-phase reactor may be from about 1 to about 30 atmospheres. A pressure of about 15 to about 25 atmospheres may be advantageously employed to facilitate separation of HCl from other reaction products, and the suitable reaction time may vary from about 1 to about 120 seconds, preferably from about 5 to about 60 seconds.

The molar ratio of HF to the amount of HCFC-243db for the vapor-phase reaction is, in one embodiment, from about the stoichiometric ratio of HF to the amount of HCFC-243db to about 50:1 and, in another embodiment, from about 10:1 to about 30:1.

In some embodiments, a catalyst is used in the reaction zone for the vapor-phase reaction of HF with HCFC-243db. Fluorination catalysts which may be used in the vapor phase reaction include carbon; graphite; alumina; fluorided alumina; aluminum fluoride; alumina supported on carbon; aluminum fluoride supported on carbon; fluorided alumina supported on carbon; magnesium fluoride supported on aluminum fluoride; metals (including elemental metals, metal oxides, metal halides, and/or other metal salts); metals supported on aluminum fluoride; metals supported on fluorided alumina; metals supported on alumina; and metals supported on carbon; mixtures of metals.

Suitable metals for use as catalysts (optionally supported on alumina, aluminum fluoride, fluorided alumina, or carbon) include chromium, iron, cobalt, nickel, ruthenium, rhodium, palladium, osmium, iridium, platinum, manganese, rhenium, scandium, yttrium, lanthanum, titanium, zirconium, and hafnium, copper, silver, gold, zinc, and/or metals having an atomic number of 58 through 71 (i.e., the lanthanide metals). In some embodiments, when used on a support, the total metal content of the catalyst will be from about 0.1 to about 20 percent by weight based on the total weight of the catalyst; in another embodiment, from about 0.1 to about 10 percent by weight based on the total weight of the catalyst.

Typical fluorination catalysts for the vapor-phase reactions in this invention include chromium-containing catalysts including chromium(III) oxide ($Cr_2O_3$); $Cr_2O_3$ with other metals such as magnesium halides or zinc halides supported on $Cr_2O_3$; chromium(III) halides supported on carbon; mixtures of chromium and magnesium (including elemental metals, metal oxides, metal halides, and/or other metal salts) optionally supported on graphite; and mixtures of chromium and other metals (including elemental metals, metal oxides, metal halides, and/or other metal salts) optionally supported on graphite, alumina, or aluminum halides such as aluminum fluoride.

Chromium-containing catalysts are well known in the art. They may be prepared by either precipitation methods or impregnation methods as generally described by Satterfield on pages 87-112 in *Heterogeneous Catalysis in Industrial Practice*, 2nd edition (McGraw-Hill, New York, 1991).

Of note are fluorination catalysts that comprise at least one chromium-containing component selected from the group consisting of crystalline alpha-chromium oxide where from about 0.05 atom % to about 6 atom % of the chromium atoms in the alpha-chromium oxide lattice are replaced by trivalent cobalt atoms, and crystalline alpha-chromium oxide where from about 0.05 atom % to about 6 atom % of the chromium atoms in the alpha-chromium oxide lattice are replaced by trivalent cobalt atoms which has been treated with a fluorinating agent. These catalysts, including their preparation, have been disclosed in U.S. Patent Application Publication US2005/0228202.

Optionally, the metal-containing catalysts described above can be pretreated with HF. This pretreatment can be accomplished, for example, by placing the metal-containing catalyst in a suitable container, and thereafter, passing HF over the metal-containing catalyst. In one embodiment of this invention, such container can be the reactor used to perform the fluorination reaction in this invention. Typically, the pretreatment time is from about 15 to about 300 minutes, and the pretreatment temperature is from about 200° C. to about 450° C.

In one embodiment of this invention, the product mixture comprises HFC-245cb, HFC-245fa, HFO-1234yf, HFO-1234ze, HCFO-1233zd and HCFO-1233xf.

Fluorination of HCFO-1233xf

In some embodiments, HCFO-1233xf may be used to make HCFC-HCFC-244bb, and/or HFO-1234yf by fluorination. These reactions are shown in FIG. 1.

In one embodiment, the reaction of HCFO-1233xf to HCFC-244bb may be carried out in the liquid phase. In another embodiment, the reaction may be carried out in the vapor phase.

In one embodiment, the reaction of HCFO-1233xf to HCFC-244bb may be carried out in batch mode. In another embodiment, the reaction may be carried out in a continuous mode.

In one embodiment, a liquid phase reaction of HCFO-1233xf to HCFC-244bb may be carried out in the presence of a catalyst. In one embodiment, the catalyst may be a Lewis acid catalyst. In one embodiment, the catalyst may be a metal-halide catalyst. In another embodiment, the catalyst may be at least one catalyst selected from the group consisting of antimony halides, tin halides, thallium halides, iron halides and combinations of two or more thereof. In another embodiment, the catalysts may be at least one catalyst selected from antimony pentachloride ($SbCl_5$), antimony trichloride ($SbCl_3$), antimony pentafluoride ($SbF_5$), tin tetrachloride ($SnCl_4$), titanium tetrachloride ($TiCl_4$), iron trichloride ($FeCl_3$), and combinations thereof. In some embodiments, the reaction may be carried out with any known fluorination catalyst for liquid phase reactions.

In one embodiment, the reaction of HCFO-1233xf to HCFC-244bb may be carried out in the absence of catalyst.

In one embodiment, a vapor phase reaction of HCFO-1233xf to HCFC-244bb may be carried out in the presence of a catalyst. In one embodiment, the reaction is carried out in the presence of a chromium-based catalyst, an iron-based catalyst, or combinations thereof. In one embodiment, the chromium based catalyst is a chromium oxide (e.g. $Cr_2O_3$). In one embodiment, the iron-based catalyst may be $FeCl_3$ on carbon.

In one embodiment, the vapor phase reaction of HCFO-1233xf to HCFC-244bb is carried out in the absence of catalyst.

Dehydrochlorination of HCFC-244bb

In some embodiments, dehydrochlorination of HCFC-244bb is used to prepare HFO-1234yf.

In one embodiment, dehydrochlorination of HCFC-244bb to HFO-1234yf is carried out in the vapor phase.

In one embodiment, vapor phase dehydrochlorination is carried out in the presence of catalyst. In one embodiment, the catalyst is selected from carbon and/or metal based catalysts. In one embodiment, the catalyst may be selected from an activated carbon, a nickel-based catalyst, a palladium based catalyst, or any combination of these catalysts. In one embodiment, the catalyst may be selected from the group consisting of Ni-mesh, palladium on carbon, palladium on aluminum oxide, or combinations thereof.

In one embodiment, HFO-1234yf is prepared by thermal dehydrochlorination of HCFC-244bb. In one embodiment, this reaction occurs in the absence of a catalyst. In one embodiment, HCFC-244bb is introduced into a reaction vessel which temperature is maintained at a temperature high enough to effect the thermal dehydrochlorination of HCFC-244bb. In one embodiment, the temperature is high enough to effect the thermal dehydrochlorination of HCFC-244bb to a percent conversion of at least 50%. In another embodiment, the temperature is high enough to effect the thermal dehydrochlorination of HCFC-244bb to a percent conversion of at least 65%. In yet another embodiment, the temperature is high enough to effect the thermal dehydrochlorination of HCFC-244bb to a percent conversion of at least 80%. In yet another embodiment, the temperature is high enough to effect the thermal dehydrochlorination of HCFC-244bb to a percent conversion of at least 70% for at least 12 hours of continuous operation.

In one embodiment, HCFC-244bb is introduced into a reaction vessel into a reaction vessel which temperature is maintained at a temperature in the range of from about 500° C. to about 700° C. In another embodiment, the temperature of the reaction vessel is maintained in the range from about 500° C. to about 650° C. In yet another embodiment, the temperature of the reaction vessel is maintained at a temperature high enough to effect the pyrolysis of HCFC-244bb to HFO-1234yf with a selectivity of 80% or greater. In yet another embodiment, the temperature of the reaction vessel is maintained at a temperature high enough to effect the pyrolysis of HCFC-244bb to HFO-1234yf with a selectivity of 85% or greater.

In one embodiment, the reaction zone is a reaction vessel comprised of materials which are resistant to corrosion. In one embodiment, these materials comprise alloys, such as nickel-based alloys such as Hastelloy®, nickel-chromium alloys commercially available from Special Metals Corp. under the trademark Inconel® (hereinafter "Inconel®") or nickel-copper alloys commercially available from Special Metals Corp. (New Hartford, N.Y.) under the trademark Monel®, or vessels having fluoropolymers linings.

In one embodiment, the HCFC-244bb is preheated in a vaporizer to a temperature of from about 30° C. to about 100° C. In another embodiment, the HCFC-244bb is preheated in a vaporizer to a temperature of from about 30° C. to about 80° C.

In some embodiments, an inert diluent gas is used as a carrier gas for HCFC-244bb. In one embodiment, the carrier gas is selected is nitrogen, argon, helium or carbon dioxide.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

General Procedure for Product Analysis

The following general procedure is illustrative of the method used for analyzing the products of fluorination reactions. Part of the total reactor effluent was sampled on-line for organic product analysis using a gas chromatograph equipped with a mass selective detector (GC/MS). The gas chromatography utilized a 20 ft. (6.1 m) long×⅛ in. (0.32 cm) diameter tube containing perfluorinated polyether sold under the trademark Krytox® by E. I. du Pont de Nemours and Company (hereinafter "DuPont") of Wilmington, Del. on an inert carbon support. The helium flow was 30 mL/min ($5.0 \times 10^{-7}$ m$^3$/sec). Gas chromatographic conditions were 60° C. for an initial hold period of three minutes followed by temperature programming to 200° C. at a rate of 6° C./minute.

Preparation of 98% Chromium/2% Cobalt Catalyst

A solution of 784.30 grams $Cr(NO_3)_3[9(H_2O)]$ (1.96 moles) and 11.64 grams $Co(NO_3)_2[6(H_2O)]$ (0.040 mole) was prepared in 2000 mL of deionized water. The solution was treated dropwise with 950 mL of 7.4 M aqueous ammonia until the pH reached about 8.5. The slurry was stirred overnight at room temperature and then evaporated to dryness in air at 110-120° C. The dried catalyst was then calcined in air at 400° C. for 24 hours prior to use.

%. The nominal catalyst bed volume was 15 cc; the contact time (CT) was 15 seconds. Examples 1 and 2 were carried out in the absence of the catalyst.

TABLE 2

Chlorofluorination of HFO-1243zf (Part A)

| Ex. No. | HF/1243/Cl$_2$ Ratio | T, ° C. | 1243zf | 243db | 244db | 1234yf | 245cb | 1233xf |
|---|---|---|---|---|---|---|---|---|
| 1 | 10/1/4 | 140 | 3.0 | 54.2 | 9.8 | 5.7 | 0 | 1.4 |
| 2$^a$ | 10/1/1 | 140 | 31.3 | 46.2 | 11.8 | 2.8 | 0 | 1.5 |
| 3$^b$ | 10/1/1 | 300 | 5.9 | 0 | 0 | 5.9 | 22.2 | 30.7 |
| 4$^c$ | 10/1/4 | 325 | 0 | 0 | 0 | 0 | 0 | 0 |
| 5 | 10/1/1 | 350 | 9.1 | 0 | 0 | 11.3 | 11.3 | 25.2 |
| 6 | 10/1/1 | 375 | 12.8 | 0 | 0 | 11.6 | 6.3 | 20.6 |

(Part B)

| Ex. No. | HF/1243/Cl$_2$ Ratio | T, ° C. | 1233zd | 1234ze | 245fa | 1223xd | 233ab | 226ba | 227ca |
|---|---|---|---|---|---|---|---|---|---|
| 1 | 10/1/4 | 140 | 7.7 | — | — | 1.0 | 6.3 | 0 | 0 |
| 2$^a$ | 10/1/1 | 140 | 1.4 | — | — | 0 | 1.3 | 0 | 0 |
| 3$^b$ | 10/1/1 | 300 | 4.1 | 2.1 | 1.3 | 20.2 | 0 | 0 | 0 |
| 4$^c$ | 10/1/4 | 325 | 0 | 0 | 0 | 0 | 0 | 23.8 | 13.9 |
| 5 | 10/1/1 | 350 | 12.4 | 4.7 | 1.9 | 18.1 | 0 | 0.2 | 0 |
| 6 | 10/1/1 | 375 | 17.6 | 6.5 | 2.3 | 16.1 | 0 | 0.2 | 0 |

$^a$243db and 244db confirmed by $^1$H and $^{19}$F NMR.
$^b$245cb and 1233xf confirmed by $^1$H and $^{19}$F NMR.
$^c$Additional products were 215aa, 216aa, 216ba, 225aa, 225ba, 226ca, 226da.

Legend

| | |
|---|---|
| 243db is CF$_3$CHClCH$_2$Cl | 244db is CF$_3$CHClCH$_2$F |
| 245cb is CF$_3$CF$_2$CH$_3$ | 245fa is CF$_3$CH$_2$CHF$_2$ |
| 1234yf is CF$_3$CF=CH$_2$ | 1233xf is CF$_3$CCl=CH$_2$ |
| 1243zf is CH$_2$=CHCF$_3$ | 233ab is CF$_3$CCl$_2$CH$_2$Cl |
| 1233zd is E- and/or Z-CHCl=CHCF$_3$ | 226ba is CF$_3$CClFCHF$_2$ |
| 1234ze is E- and/or Z-CHF=CHCF$_3$ | 227ca is CF$_3$CF$_2$CHF$_2$ |
| 1223xd is E- and/or Z-CF$_3$CCl=CHCl | 244bb is CF$_3$CFClCH$_3$ |
| 1141 is CHF=CH$_2$ | |

Examples 1-6

Chlorofluorination of HFO-1243zf

The 98% chromium/2% cobalt catalyst prepared above (21.4 grams, 15 mL, -12 to +20 mesh, (1.68 to 0.84 mm)) was placed in a ⅝" (1.58 cm) diameter Inconel® (Special Metals Corp. (New Hartford, N.Y.)) nickel alloy reactor tube heated in a fluidized sand bath. The catalyst was pre-fluorinated by treatment with HF as follows. The catalyst was heated from 45° C. to 175° C. in a flow of nitrogen (50 cc/min) over the course of about 1.5 hours. HF was then admitted to the reactor at a flow rate of 50 cc/min for 1.3 hours at a temperature of 175° C. The reactor nitrogen flow was decreased to 20 cc/min and the HF flow increased to 80 cc/min; this flow was maintained for 0.3 hour. The reactor temperature was then gradually increased to 400° C. over 1 hour. After this period, the HF and nitrogen flow was stopped and the reactor brought to the desired operating temperature. A flow of HF vapor, HFO-1243zf, and Cl$_2$ then started through the reactor. Part of the reactor effluent was analyzed by on line GC/MS.

The results of the chlorofluorination of HFO-1243zf over the 98/2 Cr/Co catalyst at various operating temperatures and indicated molar ratios of HF, HFO-1243zf and Cl$_2$ are shown in Table 2; analytical data is given in units of GC area Examples 7-11

Fluorination of HCFC-243db

The 98% chromium/2% cobalt catalyst prepared above (21.4 grams, 15 mL, -12 to +20 mesh, (1.68 to 0.84 mm)) was placed in a ⅝" (1.58 cm) diameter Inconel® nickel alloy reactor tube heated in a fluidized sand bath. The catalyst was pre-fluorinated by treatment with HF as follows. The catalyst was heated from 45° C. to 175° C. in a flow of nitrogen (50 cc/min) over the course of about 1.5 hours. HF was then admitted to the reactor at a flow rate of 50 cc/min for 1.3 hours at a temperature of 175° C. The reactor nitrogen flow was decreased to 20 cc/min and the HF flow increased to 80 cc/min; this flow was maintained for 0.3 hour. The reactor temperature was then gradually increased to 400° C. over 1 hour. After this period, the HF and nitrogen flow was stopped and the reactor brought to the desired operating temperature. A flow of HF vapor and HCFC-243db (CF$_3$CHClCH$_2$Cl) was then started through the reactor. Part of the reactor effluent was analyzed by on line GC/MS.

The results of the fluorination of HFC-243db over the 98/2 Cr/Co catalyst at various operating temperatures and indicated molar ratios of HF and HCFC-243db are shown in Table 3; analytical data is given in units of GC area %. The nominal catalyst bed volume was 15 cc; the contact time (CT) was 15 seconds. Example 7 was carried out in the absence of the catalyst.

TABLE 3

Fluorination of HCFC-243db

| Ex. No. | HF/243 Ratio | Temp. (° C.) | 1243zf | 243db | 244db | 1234yf | 245cb | 1233xf | 1233zd | 1234ze | 245fa |
|---|---|---|---|---|---|---|---|---|---|---|---|
| 7 | 5/1 | 140 | 0.1 | 88.4 | 7.4 | 0 | 0 | 3.9 | 0 | 0 | 0 |
| 8 | 10/1 | 275 | 0 | 0.2 | 0.6 | 1.3 | 4.8 | 90.0 | 0 | 0.7 | 1.0 |
| 9 | 20/1 | 325 | 0 | 0 | 0 | 19.1 | 11.4 | 61.7 | 2.3 | 3.1 | 1.9 |
| 10 | 20/1 | 350 | 0 | 0 | 0 | 32.2 | 8.1 | 45.3 | 4.7 | 7.9 | 0.9 |
| 11 | 20/1 | 400 | 0 | 0 | 0 | 17.9 | 6.6 | 36.3 | 19.7 | 14.4 | 3.6 |

Example 12

Reaction of HFC-243db with HF in the Presence of TaF$_5$

A 210 mL Hastelloy® C tube was charged with 10.0 grams (0.0599 mole) of HCFC-243db and 25.4 grams (0.040 mole) of tantalum pentafluoride. The tube was then charged with 40.0 grams (2.0 moles) of hydrogen fluoride. The tube was warmed to 150° C. and held at 149° C. to 150° C. for eight hours with shaking. The tube was then cooled to room temperature and treated with 100 mL of water. The contents of the tube were discharged and a small organic layer was collected and neutralized. The sample was 91.1% unconverted HCFC-243db; the GC-MS analysis of the converted products were as follows:

TABLE 4

| Component | GC Area % |
|---|---|
| HFC-245cb | 39.3 |
| HFC-245fa | 5.5 |
| $C_3H_3ClF_4$ | 9.2 |
| $C_3H_3ClF_4$ | 27.6 |
| HCFC-253fb | 2.9 |
| HCFC-234ab | 8.6 |
| HCFC-243fa | 6.9 |

Example 13

Fluorination of HCFO-1233xf to HCFC-244bb

The contents of a small PTFE vial containing 20 grams of viscous SbF$_5$ were poured into a dry 400 mL Hastelloy® shaker tube. The tube was closed and was pressurized with nitrogen for leak testing. The shaker tube was then cooled to less than −40° C. with dry ice, slowly vented, and then evacuated. 75 grams (3.75-moles) of anhydrous HF was condensed into the shaker tube followed by 165 grams (1.26-moles) of HCFO-1233xf. The shaker tube was placed in a barricade and shaking was started.

The shaker tube was agitated at ambient temperature (~20-23° C.) and the pressure was 21 to 25 psig. After 2 hours, shaking was stopped and 150 mL of water was carefully pumped into the shaker tube. The tube was left overnight and then cooled to 0 to 5° C. in an ice bath before depressurization and transferring the contents to a plastic container. The container was kept on ice.

The container contents were poured into a polypropylene separatory funnel containing some ice. The lower organic layer was light amber in appearance. The organic layer was separated into a media bottle made of a glass sold under the trademark of Pyrex® by Corning (Lowell, Mass.) (hereinafter "Pyrex®") containing ~50-mL of 4 molar (pH 7) phosphate buffer and ice (~100-mL). The organic layer was again separated and poured into a dry Pyrex® media bottle containing a small amount of anhydrous magnesium sulfate. Crude yield was 164.3 grams (about 120-mL, 86%).

GC/MS of the crude material showed that it was mostly HCFC-244bb. Other components included 0.13% 245cb, 0.09% 245eb, 0.16% 1233xf, and other byproducts totaling 12.2%.

Example 14

Fluorination of HCFO-1233xf to HCFC-244bb

The contents of a small PTFE vial containing 20 grams of viscous SbF$_5$ were poured into a dry 400-mL Hastelloy® shaker tube. The tube was closed and was pressurized with nitrogen for leak testing. The shaker tube was then cooled to less than −40° C. with dry ice, slowly vented, and then evacuated. 53 grams (2.65 moles) of anhydrous HF was transferred into the shaker tube followed by 227 grams (1.74 moles) of HCFO-1233xf was condensed into the chilled shaker tube. The shaker tube was placed in the barricade and shaking was started.

The shaker tube was agitated at ambient temperature (~18-21° C.) and the pressure was 16 to 20 psig. After 2 hours, shaking was stopped and 100 mL of water was carefully pumped into the shaker tube. The tube was left overnight and cooled to 0 to 5° C. in an ice bath before venting and transferring the contents to a plastic container. The container was kept on ice.

The container contents were poured into a polypropylene separatory funnel containing some ice. The lower organic layer was light amber in appearance. The organic layer was separated into a Pyrex® media bottle containing about 50 mL of 4 molar (pH 7) phosphate buffer and ice (~100-mL). The organic layer was again separated and poured into a dry Pyrex® media bottle containing a small amount of anhydrous magnesium sulfate. Crude yield was 238.8 grams (about 170-mL, 91%).

GC/MS of the crude material indicated that it was mostly HCFC-244bb. Other components included 0.11% HFC-245cb, 0.10% HFC-245eb, 0.26% HCFO-1233xf, and other byproducts totaling 9.7%.

Example 15

Example 15 demonstrates the conversion of HCFC-244bb (2-chloro-1,1,1,2-tetrafluoropropane) to HFO-1234yf (2,3, 3,3-tetrafluoropropene) in the absence of a catalyst.

An empty Inconel® tube (½ inch OD) with a heated zone of about 12 inches was heated to a temperature between 500° C. and 626° C., and HFC-244bb was fed at 0.52 mL/hour through a vaporizer set at 40° C. using a N$_2$ sweep of 2.4 sccm (4.0×10$^{-8}$ m$^3$). The reactor effluent was analyzed using an on-line GCMS, with the results being reported in mole percent.

TABLE 5

| Temp., °C. | Mole Percent | | | | | | | | |
|---|---|---|---|---|---|---|---|---|---|
| | 23 | 1141 | 143a | 245cb | 1234yf | 254eb | 244bb | 1233xf | Unks |
| 500 | 0.2 | 0.1 | 0.0 | 0.4 | 14.2 | 1.0 | 82.6 | 1.2 | 0.0 |
| 550 | 1.9 | 0.9 | 0.1 | 0.0 | 57.0 | 1.7 | 35.4 | 1.2 | 1.6 |
| 574 | 2.7 | 1.1 | 0.1 | 0.0 | 77.0 | 1.9 | 13.0 | 1.4 | 2.8 |
| 603 | 6.8 | 2.4 | 0.2 | 0.0 | 85.0 | 1.4 | 1.3 | 0.7 | 2.2 |
| 626 | 6.9 | 2.0 | 0.2 | 0.0 | 82.5 | 0.7 | 0.2 | 1.4 | 5.9 |

Example 16

Example 16 demonstrates the conversion of HCFC-244bb (2-chloro-1,1,1,2-tetrafluoropropane) to HFO-1234yf (2,3,3,3-tetrafluoropropane) in the absence of a catalyst.

An empty Inconel® tube (½ inch OD) with a heated zone of about 12 inches was heated to 575° C., and HFC-244bb was fed at 0.35 mL/hour through a vaporizer set at 40° C. using a $N_2$ sweep of 3.6 sccm ($6.0 \times 10^{-8}$ $m^3$). The reactor was operated for a total of 19 hours continuously, and samples were taken periodically and analyzed to determine % conversion of HFC-244bb, and selectivity to HFO-1234yf. The reactor effluent was analyzed using an on-line GCMS, and the data in Table 6 below is an average of at least two on-line injections at a given condition; the percentages are mole percent.

TABLE 6

| Hours | 23 | 1141 | 245cb | 1234yf | 254eb | 244bb | 1233xd | 1223 (2 isomers) | Unk |
|---|---|---|---|---|---|---|---|---|---|
| 3 | 1.9 | 0.8 | 0.1 | 68.8 | 3.5 | 17.9 | 5.1 | 0.5 | 1.3 |
| 4 | 1.4 | 0.7 | 0.0 | 61.5 | 4.2 | 22.7 | 7.4 | 1.1 | 1.0 |
| 8 | 0.0 | 0.3 | 0.0 | 61.1 | 2.6 | 15.0 | 14.1 | 3.9 | 2.8 |
| 12 | 0.0 | 0.5 | 0.0 | 60.1 | 2.0 | 13.7 | 16.4 | 6.0 | 1.3 |
| 15 | 0.9 | 0.3 | 0.0 | 66.9 | 1.7 | 14.5 | 12.0 | 2.7 | 1.0 |
| 19 | 0.0 | 0.7 | 0.0 | 67.4 | 0.0 | 7.0 | 16.6 | 8.2 | 0.0 |

Example 17

Example 17 demonstrates the dehydrochlorination of HCFC-244bb (2-chloro-1,1,1,2-tetrafluoropropane) in the presence of an activated carbon catalyst.

An Inconel® tube (½ inch OD) was filled with 4 cc (1.99 gm) of acid washed PCB Polynesian coconut shell based carbon from Calgon (6-10 mesh). HFC-244bb was fed at 1.04 mL/hour through a vaporizer set at 40° C. using a $N_2$ sweep of 2.4 sccm ($4.0 \times 10^{-8}$ $m^3$) giving a total contact time of about 32 seconds while controlling the reactor temperature at 400° C.

The data in Table 7 shows the reactor effluent composition in mole percent for this process run with an activated carbon catalyst to make HFC-1234yf via HCl elimination over the period of 7 hours of operation.

TABLE 7

| Hours | 245cb | 1234yf | 245eb | 1336 | 244bb | 1233xf | Unk |
|---|---|---|---|---|---|---|---|
| 1 | 0.0 | 52.2 | 0.2 | 0.0 | 22.4 | 10.3 | 14.9 |
| 2 | 0.0 | 44.5 | 0.2 | 0.1 | 24.6 | 13.4 | 17.3 |
| 3 | 0.0 | 38.0 | 0.2 | 0.2 | 31.9 | 14.8 | 15.0 |
| 4 | 0.0 | 25.9 | 0.2 | 0.1 | 41.8 | 15.7 | 16.3 |
| 5 | 0.0 | 15.5 | 0.3 | 0.1 | 49.4 | 17.9 | 16.7 |
| 6 | 0.5 | 7.1 | 0.3 | 0.1 | 53.8 | 18.0 | 20.2 |
| 7 | 0.6 | 2.9 | 0.3 | 0.1 | 54.2 | 17.3 | 24.5 |

What is claimed is:

1. A composition comprising HFO-1234yf, HFO-1234ze, HFO-1243zf and at least one additional compound selected from the group consisting of HCFO-1233xf, HCFC-244bb and HCFC-1131.

2. The composition of claim 1 containing less than about 1 weight percent of the at least one additional compound.

3. The composition of claim 1 wherein said additional compound comprises HCFO-1233xf.

4. The composition of claim 1 wherein said additional compound comprises HCFC-1131.

5. The composition of claim 1 wherein said additional compound further comprises HFC-143a.

6. The composition of claim 1 wherein said additional compound comprises HCFC-244bb.

7. The composition of claim 2 wherein said additional compound comprises HCFO-1233xf and HCFC-1131.

8. The composition of claim 7 wherein the amount of the at least one additional compound is greater than 0 and less than about 1 weight percent.

9. A composition comprising HFO-1234yf, HFO-1234ze, HFO-1243zf, HCFC-1131 and HFC-143a.

10. A composition comprising HFO-1234yf, HFO-1234ze, HFO-1243zf, HCFC-1131, HFC-143a and at least one additional compound selected from the group consisting of HCFC-244db, HFC-245cb and HFC-245fa.

11. The composition of claim 10 wherein the amount of the at least one additional compound is greater than 0 and less than about 1 weight percent.

12. The composition of claim 11 wherein the additional compound comprises HCFC-244bb.

13. The composition of claim 11 wherein the additional compound comprises HFC-245cb.

14. The composition of claim 11 wherein the additional compound comprises HFC-245fa.

15. A method for carrying heat from a heat source to a heat sink wherein a media comprising the composition of claim 1 is used as heat transfer fluid.

16. A heat transfer system comprising at least one member selected from the group consisting of air conditioners, freezers, refrigerators, heat pumps, water chillers, flooded evaporator chillers, direct expansion chillers, walk-in coolers, heat pumps, mobile refrigerators, mobile air conditioning units and combinations thereof, and wherein the system comprises a working fluid comprising the composition of claim 1.

17. The heat transfer system of claim 16 wherein the system comprises a mobile refrigeration apparatus.

18. A method for carrying heat from a heat source to a heat sink wherein a media comprising the composition of claim 9 is used as heat transfer fluid.

19. A method for carrying heat from a heat source to a heat sink wherein a media comprising the composition of claim 10 is used as heat transfer fluid.

\* \* \* \* \*